(12) United States Patent
Liu

(10) Patent No.: US 6,229,027 B1
(45) Date of Patent: May 8, 2001

(54) PROCESS FOR MANUFACTURING PACLITAXEL AND 13-ACETYL-9-DIHYDROBACCATIN IV

(76) Inventor: Jian Liu, 470 Cherry Avenue, Fredericton, New Brunswick (CA), E3A 5N9

(*) Notice: Subject to any disclaimer, the term of this patent is extended or adjusted under 35 U.S.C. 154(b) by 0 days.

(21) Appl. No.: 09/522,625

(22) Filed: Mar. 10, 2000

(51) Int. Cl.[7] .................................................. C07D 305/14
(52) U.S. Cl. .............................................................. 549/510
(58) Field of Search ............................................... 549/510

(56) References Cited

U.S. PATENT DOCUMENTS 5,380,916 * 1/1995 Rao ...................................... 560/107
6,136,989 * 10/2000 Foo et al. ............................. 549/510

OTHER PUBLICATIONS

Witherup, K. M. et al "Taxus spp. needles contain amounts of taxol comparable to the bark of *taxus brevifolia*" J. Nat. Prod. vol. 53 No. 5 pp. 1249–1255, 1990.*

* cited by examiner

*Primary Examiner*—Howard C. Lee
*Assistant Examiner*—Leigh C. Maier
(74) *Attorney, Agent, or Firm*—Paul S. Sharpe; Marks & Clerk

(57) ABSTRACT

A process for obtaining paclitaxel and other taxanes from a source containing taxanes. The process involves extracting taxane compounds from the source into an organic solvent and passing this composition through a distribution chromatography column and eluting taxane compounds with the dry distribution column. The eluted taxane compounds are isolated by further processing techniques.

8 Claims, No Drawings

PROCESS FOR MANUFACTURING PACLITAXEL AND 13-ACETYL-9-DIHYDROBACCATIN IV

FIELD OF THE INVENTION

The present invention relates to the production of paclitaxel from pacific yew, ornamental yew, or other yew species', needles, barks and roots and more particularly, the present invention relates to a process for extracting paclitaxel economically which is presently extracted by a high cost process due to an extremely high percentage of unwanted impurities carried forward in the extract during the extraction.

BACKGROUND OF THE INVENTION

In the prior art there is described an extraction method (Journal of Natural Products 53, 1249–55, 1990), which reported that paclitaxel content in the extract in the range of between 0.009% and 0.07%. After removing the hexanes soluble impurities (waxes, pigments, etc.) and after partition between water and dichloromethane, the paclitaxel concentration in the dichloromethane soluble crude extract was in the range of between 0.03% and 0.3% by weight. Paclitaxel (Taxol) is represented by the following structural formula:

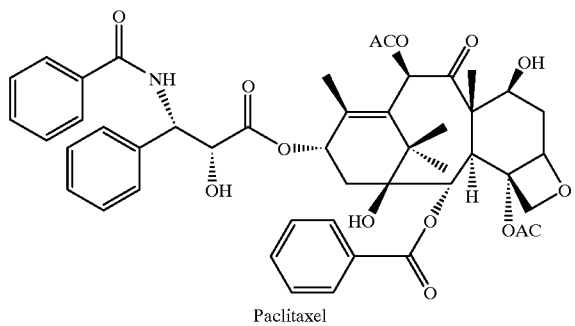

Paclitaxel is an anticancer compound. Paclitaxel exhibits a unique mechanism for preventing the growth of cancer cells by affecting the microtubules, which plays an important role in cell division and other cellular functions.

Paclitaxel is clinically effective for the treatment of refractory human ovarian and breast cancer and has exhibited promising activity against a number of other types of cancers such as liver, peritoneal, cervical, prostate, colon, and esophageal cancers.

Paclitaxel was primarily extracted from the bark of pacific yew *Taxus brevifolia*. Unfortunately, the yew grows very slowly, approximately eight inches per year and thus the bark is a limited source of paclitaxel. This lead researchers to seek alternative means for producing paclitaxel and analogues thereof which may display superior antitumor activity, such as derivatives of 9-dihydrotaxol that have enhanced water solubility. As an example 13-acetyl-9-dihydrobaccatin III, a taxane diterpene, has been found to be a useful precursor to make such analogues. This has been discussed in U.S. Pat. No. 5,440,056, issued to Klein et al., Aug. 8, 1995.

13-Acetyl-9-dihydrobaccatin III and baccatin III are represented by the following structure formulas:

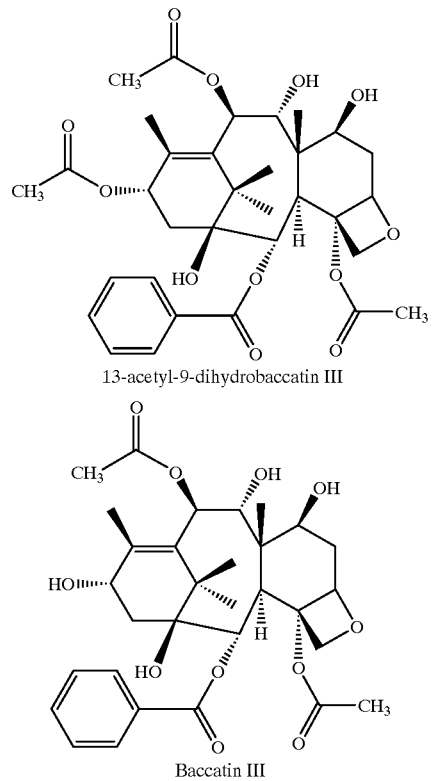

13-acetyl-9-dihydrobaccatin III

Baccatin III

This can be obtained from, for example, *Taxus canadensis* which is more widely distributed than *Taxus brevifolia*. Hence, 13-acetyl-9-dihydrobaccatin III is available more abundantly than paclitaxel.

Conventional methods for the isolation of taxanes, including paclitaxel, 13-acetyl-9-dihydrobaccatin III, and baccatin III generally involve the steps of extracting taxanes from a biomass with an alcoholic solvent and separating and purifying the individual taxane by chromatography.

Prior art methods disclose the use of various types of chromatographic technologies to separate paclitaxel and derivatives thereof. For example, U.S. Pat. No. 5,380,916, issued to Rao, Jan. 10, 1995, describes a process using C18 reverse phase liquid chromatography. Although reverse phase chromatography can be successful in separating the taxanes, this protocol employs an expensive absorbent and requires a significant time investment. Accordingly, this process is not economically and industrially viable.

U.S. Pat. No. 5,478,736, issued to Nair, Dec. 26, 1995, discloses a process using a silica gel normal phase absorption chromatography to purify taxanes. In normal phase absorption chromatography, $Al_2O_3$ or silica gel is used as an absorbent which is about 100 times less expensive than the ordinary reverse phase absorbent. The problem for the normal phase silica gel absorption chromatography is that the absorbent will bind with paclitaxel which will not be eluted by solvent mixture, therefore the product yield is reduced.

U.S. Pat. No. 5,530,020, issued to Gunarvardana et al., Jun. 25, 1996, disclosed a process for isolating 13-acetyl-9-dihydrobaccatin III from *Taxus canadensis* which employs planet coil countercurrent chromatography (PCCC). Some of the disadvantages associated with this procedure are that it is complex, consumes significant amounts of solvent and can be used to purify only a small amount (milligrams) of samples.

So far, no distributive column chromatography for separating and purifying paclitaxel and related taxanes has been disclosed.

SUMMARY OF THE INVENTION

An object of the present invention is to provide an improved method for isolating taxanes, particularly paclitaxel, 13-acetyl-9-dihydrobaccatin III, from a taxus species.

One aspect of the present invention, there is provided a method for isolating taxane from a crude extract of a taxus species comprising the step of subjecting the crude extract to dry column chromatography and distributive column chromatography.

The method of the present invention may be practiced on a small laboratory scale as well as large industry scale.

Conveniently, the taxane is obtained from extraction of the plant material with an alcoholic solvent at refluxing. Preferably, the column to be used with the method of the present invention includes a nylon tube packed with pretreated silica gel, having a micro sphere size of between 150 mesh and 250 mesh for using as dry column distribution chromatography.

A glass column packed with pretreated silica gel having a particle size of between 150 mesh and 250 mesh for using as wet distributive column chromatography.

In one embodiment of the invention, the method includes the steps of dry column distribution chromatography to obtain 13-acetyl-9-dihydrobaccatin III, normal phase distributive column chromatography to obtain paclitaxel and baccatin III.

In another embodiment of the invention, 13-acetyl-9-dihydrobaccatin III can be purified by dry column distribution chromatography with eluting solvent hexanes and ethyl acetate (4:6).

In another embodiment of the invention, paclitaxel may be further purified by normal phase distributive column chromatography. Preferably, the eluting solvent for this step is hexane:ethyl acetate (starting from 6:4 ending at 3:7). This chromatography may be repeated several times if necessary.

In accordance with another aspect of the present invention, this is provided a method for obtaining taxanes from a Taxus species, including, but not limited to *T. brevifolia, T. baccata, T. cuspidata, T canadensis, T. wallichiana, T. chinensis, T. funanesis,* T. X media ov. densiformis and T. X media ov. Hicksii.

The process comprises the steps of extracting a source material using alcoholic solvent concentrated the alcoholic extract to get a taxanes containing residue, partitioning the residue was partitioned between water and $CH_2Cl_2$, then concentrating $CH_2Cl_2$.

Solution to get a taxane rich residue, separating the taxanes into taxane containing fractions by subjecting the taxanes rich residue to dry column distribution chromatography in a dry chromatography column, and recovering any individual taxane from the column.

In another embodiment of the present invention, paclitaxel and baccatin III may further be purified by the steps of crystallizing the 13-acetyl-9-dihydrobaccatin III out of the taxane-containing solution with an alcoholic solvent to obtain 13-acetyl-9-dihydrobaccatin III, and purifying the paclitaxel-containing solution by normal phase column distribution chromatography.

The advantages of the present invention are to provide a method for the isolation of taxanes which is quick, easy to perform, cost-effective and efficient, both in small and large scale productions.

DETAILED DESCRIPTION OF THE PREFERRED EMBODIMENT

The starting material for this invention is a plant material selected from species of taxus, particularly *Taxus canadensis.*

The taxanes can be obtained from barks, needles, roots, stems and wood or mixture thereof. Desirably, the twigs or needles or mixture of them are used. The biomass used may be dried or fresh.

The biomass is ground and extracted with a polar solvent such as an alcohol, desirably methanol. The extractions continues at refluxing for 3 hours and is filtered. The residue is extracted again at refluxing for 2 hours and is filtered. The extract is combined and concentrated to about 5% of the original volume by evaporation. The paclitaxel content in this concentrate is between 0.2% and 0.3% by HPLC area percent. About 2 equal amounts of water is added to the concentrate. The aqueous solution is extracted several times with dichloromethane and then the aqueous layer is discarded. The organic layer is concentrated to a small volume. The paclitaxel content in this residue is approximately 1%. The residue is subjected for dry column distribution chromatography.

Dry Column Chromatography (DCC) provides an alternate method to Thin Layer Chromatography (TLC) and preparative column chromatography. The cost is much less compared to that of preparative Liquid Chromatography (LC). Samples which are separable on silica gel or neutral alumina TLC plates can also be separated by DCC. One of the advantages of DCC is the direct transferability of the conditions from TLC to DCC. All work done to determine the conditions for separation of samples on DCC can be done preliminarily on TLC plates. Once determined, these conditions can be applied to DCC which will give a degree of separation similar to that obtained on the thin-layer plate. DCC provides the further advantage that the number of fractions to be processed depends on the number of cuts made which does not usually exceed fifteen, and most often, does not exceed ten cuts, which is in contrast to the "liquid-flow" columns which can require a large (>50) number of fractions to be collected. Another advantage of DCC is the use of nylon tubing as column and fluorescent absorbents which provides simplified detection and isolation procedures. Therefore, compared to the "liquid-filled" column chromatography, dry column chromatography is often a quicker, easier and less expensive technique.

The process for dry column chromatography is generally set out in "Progress in Separation and Purification", Marjorie, M., E. S. Perry and C. J. Van Oss Ed., John Wiley & Sons, 1970, volume 3, pages 73–95.

Briefly, the general procedures for accomplishing dry column chromatography involve the use of a column including a nylon tubing, but other types of tubes such as glass may also be used. The tube is placed in acetone overnight and air dried to remove any solvent. The column is prepared by sealing the tubing at one end, and inserting a small pad of cotton or glass wool from the other end. The sealed end of the tubing is pierced to provide vent, and the tubing is dry packed with alumina trioxide or silica gel until it is sturdy enough to stand upright in a clamp. The sample may be poured directly onto the tube or dissolved in a small volume of the solvent to be used for development, and then distributed evenly on the top of the column. Alternatively, the sample may be coated onto a small amount of adsorbent, dried, ground and then added to the top of the column. The sample is passed down the column with an eluting solvent. A constant liquid head of solvent of about one to two centimeters should be maintained at all times. The column should never run dry.

It has been found that the process of the present invention requires 3 to about 5 hours to complete the separation of the desired compounds. Although the separation time is slower than the usual small scale laboratory process. DCC is still a faster technique than "liquid-filled" chromatography which can take three to five days to complete. Separation is achieved as the mixture runs down the column. When the mixture reaches the base of the column, the development is stopped and the ends of the column are sealed. The various components of the extract can be identified by the separate bands which can be detected by, for example, a UV or visible method. The column is then cut into the desired sections and the pure compounds are eluted with suitable solvents.

The present invention can be best practiced using a nylon column. Alumina trioxide or silica gel are suitable supporting agents, here, silica gel being preferred. In absorption chromatography, the silica gel contains silylhydroxide groups (—SiOH) which bind with the polar group of the solute. Thus the more polar compounds move more slowly along the column than less polar compounds. In the reverse phase chromatography, the surfaces of silica gel have been modified by various functional groups, which bind with non-polar group of the solute. Thus the more polar compounds move more faster along the column than less polar compounds. The disadvantage of the reverse phase chromatography is that the process is more expensive and time consuming than normal phase chromatography. But both processes all belong to absorption chromatography.

The normal phase absorption chromatography is such that paclitaxel is not cleanly separated, the process need be repeat as many as 10 times to reach the final purity of paclitaxel because of the large number of impurities in the crude extract.

The present invention using a new chromatography process, which is called normal phase distribution chromatography, to separate and purify paclitaxel and related taxanes.

In this distributive column chromatography, the silica gel used is pretreated with formamide. The (—SiOH) groups of the silica gel have been binded with (H—C=O—NH$_2$) by hydrogen bond or Van der Waals forces between —SiOH and H—C=O—NH$_2$ groups. Thus the silica gel has lost its absorption properties and used only as the carriers of formamide (FAM).

The material to be separated will be distributed between formamide and the eluting solvent according to their polarity. The chromatographic behaviors are similar to the normal phase chromatography, thus the more polar compounds move more slowly along the column than less polar compounds.

For the Dry Distributive Column Chromatography

The silica gel or alumina trioxide are treated according to the following method:
1) The silica gel to be used mixed with excess 10% to about 15% FAM in Me$_2$CO, the mixture is stirred for 15 minutes at room temperature, then filtered. The filtrate was concentrated to recover the solvent, the residue was discarded.
2) The silica gel was then air dried to remove all solvent. The air dried silica gel is ready to use.

For the Wet Distributive Column Chromatography

The silica gel to be used is mixed with excess between 10% and 15% formamide in acetone. The mixture is stirred for 15 minutes at room temperature, then poured into a column. The excess solvents are flowed passing the column until about 1 cm to 2 cm of solvent head is over the packed silica gel bed. The column is kept at room temperature for a few hours before adding samples on the top of the column.

The present invention can be best practiced using nylon columns. Alumina trioxide or silica gel are suitable carriers, silica gel being preferred.

Silica gel normally has a functional group of —SiOH surrounding its surface. When it was treated with H—C=O—NH$_2$ (formamide) some kind of hydrogen bond formed between the —SiOH functional group and formamide, as well as some other interactive forces, therefore, the silica gel has no longer maintained its absorption properties, it is a carrier of formamide only. In the surface of silica gel particle, a fine thin film of formamide formed, which is called stationary phase.

The distribution chromatography differs from traditional absorption chromatography. In the traditional absorption chromatography the system consisted with absorbent (stationary phase), eluting solvent/s (mobile phase) and solute, therefore the system is a three components system. In distribution chromatography, the chromatography systems consist with supporter (carrier), polar solvent (stationary phase), eluting solvent/s (mobile phase), and solute, therefore, the system is a four components system.

The separation mechanism is different in the two chromatographic systems. In absorption chromatography, the material is separated as a result of repeated sorption/desorption steps during the movement of the sample components along the stationary bed, and the separation is achieved due to differences in the sorption/desorption equilibrium constants of the individual sample components.

In the distribution chromatography, the material to be separated are separated as a result of distribution different in two insoluble liquid phases, and the separation is achieved due to differences of distribution constants in the two insoluble liquid phases of the individual sample components.

Generally, distribution chromatography is used to separate polar compounds, such as sugars, peptides, glycosides and other polar compounds.

In the present invention, it has been found that the distribution chromatography achieves excellent separation for taxane diterpene relative to absorption chromatography, including normal phase and reverse phase chromatography.

The present invention can be best practiced using nylon column dry packed with pretreated silica gel for isolation of 13-acetyl-9-dihydrobaccatin III. The silica gel has a micro sphere size of between 150 mesh and 250 mesh. The dimensions of the column are 12 inches×120 inches. The amount of silica gel required is, in turn, determined by the sample side. When practicing the dry column distribution chromatographic separation of the present invention, it has been found that the ratio of sample size to the amount of silica gel required to separate the taxanes ranges from between 1:15 and 1:20, desirably 1:20. Hence, the amount of silica gel needed is approximately fifteen to twenty times, and desirably twenty times the amount of sample. The above ratios have been found to be optimal with respect to the cost and degree of separation. Augmenting the amount of silica gel used will increase the cost which can be substantial in large scale process. On the other hand, reducing the amount of silica gel will result in a poor separation.

Having described the dry column distribution chromatographic techniques and conditions suitable for the present invention, a preferred experiment of the method for isolating taxanes in accordance with the present invention follows.

The crude dichloromethane extract is separated into several individual taxanes by charging the crude extract onto the top of the column, and adding a solvent mixture of hexanes and ethyl acetate (4:6) thereto. Once the solvent reaches the bottom of the column, the eluting is stopped and the nylon tube is closed, then the column is sliced into various sections. The compounds from the sliced sections are washed with a polar solvent such as an alcohol, such as methanol. The individual taxanes were identified by TLC.

13-Acetyl-9-dihydrobaccatin III is obtained by crystallizing from methanol. The crystallization normally continues overnight at room temperature.

Paclitaxel is separated from other taxanes by purification as follows. The fractions are analyzed by TLC. Paclitaxel shows a purple green color spot and 13-acetyl-9-dihydrobaccatin III shows a dark green color spot on the TLC plate by spraying 10% $H_2SO_4$ ethanol solution.

The fractions containing paclitaxel are combined, and concentrated to dryness, and the residue is dissolved with $CH_2Cl_2$. The $CH_2Cl_2$ solution is purified by wet column distribution chromatography. The column is packed with pretreated silica gel having micro sphere size of between 150 mesh and 250 mesh, and operating at a pressure of 30 p.s.i. Useful elutants for this invention can be selected from the mixture of hexanes and ethyl acetate, or from the standard texts of chromatography, for example, hexanes and acetone.

A gradient solvent system of hexanes and ethyl acetate, which in a ratio of hexanes to ethyl acetate of about 5:5 to 3:7, is found to be particularly useful for the purpose of separating paclitaxel from close related taxanes. The taxanes containing fractions are collected from the column, and the one containing paclitaxel are combined and concentrated to remove the solvent. The residue was dissolved in methanol and about 30% equivalent of water was added. The aqueous solution was kept at room temperature overnight, the crystals formed were filtered out and dried in a vacuum oven at 70° C. Paclitaxel is obtained as a cream colored powder.

The fractions containing baccatin III are combined and concentrated to dryness. The residue is dissolved in methanol. The methanol solution is kept in a refrigerator overnight. Baccatin is obtained as off white crystal, which is further recrystallized by dissolving the solids in small volumes of acetone. The acetone solution is diluted with the equivalent hexanes, and the mixture is allowed to sit at room temperature overnight to yield baccatin III as white needle-like crystals.

EXAMPLE 1

To approximately 350 kg of dried ground needles and twigs of *Taxus canadensis* in an industrial multi-functional extractor, 1200 liters of methanol were added. The mixture was refluxed for 3 hours and filtered. The raw material was then refluxed for 2 hours with 900 liters of methanol and then the methanol solution was filtered again. The filtrate was combined and concentrated to approximately 150 liters under vacuum in a spray evaporator, then one equivalent of water was added to dilute the concentrate. The aqueous solution was partioned between water and methylene chloride (450 L, 1:1) in a 1000 L reactor which is equipped with an electric stirrer. The mixture was stirred for 5 minutes at a speed of 80/min, then kept at room temperature for 1 hour or until the mixture becomes two layers. The organic layer was collected and the aqueous layer was extracted two more times with 400 liters of methylene chloride (200 liters each). The methylene chloride solution was combined and concentrated in a thin film evaporator which is equipped with two cyclone separators under a vacuum to become a slurry form.

EXAMPLE 2

To approximately 70 kg of silica gel in a 500 liter mixer equipped with an electric stirrer, 250 liters of 15% formamide in acetone were added, and the mixture was stirred for 15 minutes at room temperature, then the mixture was kept at room temperature for another 30 minutes and filtered. The solid silica gel was collected and air dried in a shelve dryer, the filtrate was concentrated to recover the solvent, acetone and excess formamide.

EXAMPLE 3

Dry Column Distribution Chromatography

The pretreated silica gel from example 2 was packed in a nylon tube having dimension of 9 inches×120 inches with a wall thickness of approximately 0.1 mm. The silica gel used has a micro sphere size of between 150 mesh and—250 mesh. The nylon column was then placed into a same size stainless steel column to hold the weight of the nylon column. The elutant used was a mixture of hexane and ethyl acetate (4:6), other organic solvent which insoluble in formamide may be used.

The sample from example 1 (6 kg, approximately 70% solid mass) was diluted with 5 liters of ethyl acetate, and then was placed on the top of the nylon column, and the column was subjected for dry column distribution chromatography.

The column was developed with hexanes: ethyl acetate (4:6), being careful to keep a constant one to two cm of liquid head at all times, once the elutant reached the bottom of the column, further column development was stopped. The nylon column was taken out from the holding stainless steel column and then was cut into 15 portions. Each portion was checked by TLC analysis (samples were sprayed with 10% $H_2SO_4$ in ethanol followed by heating at 100–105° C. for a couple of minutes). It was found that 13-acetyl-9-dihydrobaccatin III and baccatin III moved faster than paclitaxel along the column and the chromatographic behavior in the distribution chromatography differed from the one normal phase absorption chromatography and similar as in the reverse phase absorption chromatography.

The 13-acetyl-9-dihydrobaccatin III, baccatin III, and paclitaxel containing portions were placed into 6 inch short glass columns and washed with methanol, respectively. The methanol solutions were collected and then concentrated to dryness separately.

The 13-acetyl-9-dihydrobaccatin III portion residue was dissolved in small amounts of methanol (the amount of methanol was good enough to dissolve the residue at 60° C.), and the methanol solution was cooled at room temperature and then kept overnight at room temperature. The crystals formed were filtered out and washed with acetone and then dried in a vacuum oven at 80° C. to yield 13-acetyl-9-dihydrobaccatin III, as needle-like crystals (approximately 120 g), which is identified by NMR spectros copies.

$^1$H-NMR (400 MH$_2$, CDCl$_3$): δ8.07 (d, 2H, $2^1$, $6^1$-Ar—H), 7.58 (dd, 1H, $4^1$-Ar—H), 7.45 (dd, 2H, $3^1$, $5^1$-Ar—H), 6.17 (d, H-10), 6.14 (dd, H-13), 5.73 (d, H-2), 4.93 (d, H-5), 4.41 (dd, 2H, H-7, 9), 4.28 (d, H-20a), 4.14 (d, H-20b), 3.02 (d, H-3), 2.51 (ddd, H-6a), 2.26 (S, 10-OAc), 2.18 (m, 2H, H-14), 2.17 (S, 4-OAc), 2.12 (S, 13-OAc), 1.91 (dd, H-6b), 1.91 (S, 18-CH$_3$), 1.79 (S, 19-CH$_3$), 1.66 (S, 16-CH$_3$), 1.23 (S, 17-CH$_3$) ppm.

13C-NMR (100 MH$_2$, CDCl$_3$): δ170.55, 170.48, 169.38, 167.00, 139.58, 134.88, 133.69, 130.05, 129.18, 128.62, 84.03, 82.05, 78.74, 76.77, 76.55, 73.91, 73.49, 73.18, 69.74, 47.07, 44.84, 43.00, 37.92, 35.92, 28.27, 22.84, 22.56, 21.34, 21.24, 14.86, 12.48 ppm.

EXAMPLE 4
Normal Phase Absorption Chromatography

The baccatin containing portion residue from example 3 was dissolved in small amount of dichloromethane (only a sufficient amount to dissolve the material at warming of the solvent), then the dichloromethane solution was subjected for a normal phase flash chromatography. A 10 cm×150 cm glass column was used. The column packed with silica gel (150 mesh and 250 mesh). The eluting solvent was a decreasing gradient system of hexane and acetone (starting from 70:30 and progressing to 45:55). Fractions of 1000 ml were collected. The fractions containing baccatin III were combined and concentrated to dryness. The residue was dissolved in 1000 ml of methanol and kept at room temperature overnight. Some white crystals were formed. The crystals were filtered and recrystallized from methanol. 23 g of white crystals were obtained and identified by comparison with a reference sample over HPLC as baccatin III.

EXAMPLE 5
Normal Phase Distribution Chromatography

The paclitaxel containing portion residue from example 3 was dissolved in a small amount of ethyl acetate and diluted with a small amount of hexane. 20 kg of silica gel was treated as disclosed in example 1 and then mixed with 40 liters of mixed solvents of hexane and ethyl acetate (6:4), then the mixture was poured into a 15 cm×150 cm low pressure preparative column. The excess solvent was allowed to flow out until 1 cm of solvent head remained on the top of the column. The sample solution was carefully added to the top of the silica gel bed. The column then was eluted with a gradient solvent system of hexane and ethyl acetate (starting from 6:4 and ending at 3:7). Fractions of 2000 ml each were collected, and the flow rate was between 75 ml/min and 100 ml/min.

The fractions containing paclitaxel were combined and concentrated to remove most of the solvent, the residue was then dissolved in methanol (1500 ml). To the methanol solution approximately 30% of the volume of water was added, then the aqueous solution was kept at 5° C. overnight. The crude crystalline solid from the aqueous methanol solution was filtered out and dried in a vacuum over at a temperature of between 75° C. and 80° C. The solid consisted of approximately 70% paclitaxel and 23% of cephalomanine and other unidentified taxanes. The yield was 66 g.

EXAMPLE 6
Macroreticular Adsorbent Resin Absorption Chromatography 50 g of crude paclitaxel from example 5 was dissolved in 350 ml of acetone, then mixed with 200 g of polymethacrylate-divinyl benzene co-polymer resin. The mixture was placed into a round bottom flask and then evaporated over a rotary evaporator to remove the acetone. The coated material was then placed on the top of a low pressure preparative column. Column size is 100 cm×150 cm and packed with polymethacrylate-divinyl benzene co-polymer resin. The polymer resin particle size is between 75 μm and 150 μm. The co-polymer resin was prepared from Amberlite® IRP64. After the sample was added the column top opening was sealed and eluted with a step gradient of solvent mixture of acetone and water (starting acetone:water 3:7 and ending at 65:35). The column was operated under the pressure of 30 p.s.i. The change of solvent was monitored by the results of the TLC and HPLC analytic results of the fractions.

Fractions of approximately 1000 ml/each were collected and monitored by TLC and HPLC analysis. The flow rate was 100 ml/min. The paclitaxel containing fractions were combined and were allowed to stand at 5° C. until crystallization of the compound was completed.

The crystals were filtered out and recrystallized from 65% methanol in water to yield white crystals (30.5 g) with purity greater than 99%. Identification of paclitaxel as follows:

1H-NMR (400 MH$_2$, CDCl$_3$): δ8.12 (d, 2H, Ar—H), 7.73 (d, 2H, Ar—H), 7.61 (dd, Ar—H), 7.51 (m, 5H, Ar—H), 7.41 (m, 4H, Ar—H), 7.38 (dd, Ar—H), 6.98 (d, N—H), 6.27 (S, H-10), 6.23 (dd, H-13), 5.78 (dd, H-3$^1$), 5.67 (d, H-2), 4.94 (d, H-5), 4.79 (dd, H-2$^1$), 4.40 (dd, H-7), 4.30 (d, H-20a), 4.19 (d, H-20b), 3.79 (d, H-3), 3.54 (d, —OH), 2.51 (ddd, H-6a), 2.46 (d, —OH), 2.38 (S, 4-OAc), 2.33 (m, H-14), 2.24 (S, 10-OAc), 1.89 (ddd, H-6b), 1.79 (S, 18-CH$_3$), 1.68 (S, 19-CH$_3$), 1.24 (S, 16-CH$_3$), 1.14 (S, 17-CH$_3$) ppm.

13C-NMR (100 MH$_2$, CDCl$_3$): δ203.60, 172.69, 171.25, 170.33, 166.97, 141.94, 137.91, 133.70, 133.56, 133.14, 131.97, 130.18, 129.09, 129.02, 128.68, 128.36, 127.00, 84.37, 81.13, 79.00, 77.18, 76.48, 76.26, 75.53, 74.89, 73.14, 72.38, 72.17, 58.59, 54.98, 45.56, 43.14, 35.64, 35.57, 26.84, 22.61, 21.79, 20.83, 14.83, and 9.53 ppm.

EXAMPLE 7

The bromination was carried out in accordance with using a method of U.S. Pat. No. 5,969,165.

The crude paclitaxel from example 5 (10 g) was dissolved in 100 ml of dichloromethane and dichloromethane solution was poured into a 500 ml three neck round bottom flask. The solution was stirred at room temperature for a few minutes, then 5 equivalent of bromine (5 equivalent mole ration of bromine vs cephalomanine) was added dropwise over 1 hour. The reactants were stirred at room temperature until the reaction was completed (approximately 2–3hours), monitored by TLC analysis. Once the reaction was completed, the solution was diluted with 300 ml of CH$_2$Cl$_2$, and was transferred to a separation funnel. To the solution 300 ml of 10% aqueous sodium thiosulphate (Na$_2$S$_2$O$_3$) was added to absorb any excess bromine (Br$_2$). The dichloromethane layer was separated and washed with water and brine, then concentrated to dryness under vacuum to yield a light brown powder.

EXAMPLE 8
Separation of Paclitaxel by Distribution Chromatography

The crude reactants (10 g) from example 7 was dissolved in 50 ml of ethyl acetate and then diluted with 50 ml of hexane. The sample solution was added to the top of a low pressure glass column (5×100 cm). The column was packed with pretreated silica gel and subjected for distribution column chromatography. Using similar apparatus and methodology as used in example 5, paclitaxel was finally obtained as white needle-like crystals with a purity greater than 99% (by HPLC area percent). Yield was found to be 6.1 g.

Although embodiments of the invention have been described above, it is not limited thereto and it will be apparent to those skilled in the art that numerous modifications form part of the present invention insofar as they do not depart from the spirit, nature and scope of the claimed and described invention.

I claim:

1. A method of isolating taxane compounds from a source containing taxane compounds, comprising the steps of:
   providing a source containing taxane compounds;
   extracting said taxane compounds into an organic solvent;
   providing a distribution chromatography column;
   providing dry carrier material within said colunm, resulting in a dry distributuion column;
   providing an elutant;
   eluting said source of taxane compounds with said elutant in said dry distribution column;
   eluting at least 13-acetyl-9-dihydrobaccatin, baccatin III, baccatin III and paclitaxel; and
   isolating said 13-acetyl-9-dihydrobaccatin, baccatin III, baccatin III and paclitaxel.

2. The method as set forth in claim 1, including washing said 13-acetyl-9-dihydrobaccatin III, baccatin III and paclitaxel with methanol.

3. The method a set forth in claim 1, wherein said step of isolating includes dissolving said baccatin III in dichloromethane.

4. The method as set forth in claim 3, further including eluting said baccatin III in dichloromethane in a normal phase flash chromatography column.

5. The method as set forth in claim 4, including employing an elutant containing hexane and acetone.

6. The method as set forth in claim 1, wherein said step of isolating includes dissolving said paclitaxel in a solution of ethyl acetate and hexane.

7. The method a set forth in claim 6, including eluting said solution containing paclitaxel in a low pressure preparative column.

8. The method as set forth in claim 1, wherein said source of taxanes includes at least one of *Taxus brevifolia, Taxus brevifolia, Taxus baccata, Taxus cuspidata, Taxus canadensis, Taxus wallichiana, Taxus chinensis* and *Taxus funanesis*.

* * * * *